US005458616A

United States Patent [19]
Granger et al.

[11] Patent Number: 5,458,616
[45] Date of Patent: * Oct. 17, 1995

[54] SILICONIZED SURGICAL NEEDLE AND METHOD FOR ITS MANUFACTURE

[75] Inventors: Richard N. Granger, Huntington; Ross R. Muth, Brookfield; George R. Proto, West Haven, all of Conn.

[73] Assignee: United States Surgical Corporation, Norwalk, Conn.

[*] Notice: The portion of the term of this patent subsequent to Nov. 21, 2010 has been disclaimed.

[21] Appl. No.: 313,666

[22] Filed: Sep. 27, 1994

Related U.S. Application Data

[63] Continuation of Ser. No. 144,930, Oct. 28, 1993, abandoned, which is a continuation of Ser. No. 23,734, Feb. 22, 1993, Pat. No. 5,258,013, which is a continuation of Ser. No. 638,169, Jan. 7, 1991, abandoned.

[51] Int. Cl.$^6$ ................................................ A61B 17/04
[52] U.S. Cl. ...................... 606/223; 606/224; 427/372.2; 427/421; 427/427; 428/450
[58] Field of Search ..................................... 606/223–224; 427/372.2, 421, 427; 428/450; 524/588, 731, 862, 418

[56] References Cited

U.S. PATENT DOCUMENTS

| 3,574,673 | 4/1971 | Schweiger | 428/450 |
|---|---|---|---|
| 3,767,385 | 10/1973 | Slaney | 148/11.5 N |
| 3,816,920 | 6/1974 | Sastri | 30/346.54 |
| 3,957,713 | 5/1976 | Jeram et al. | |
| 4,445,991 | 5/1984 | Arbit | |
| 4,477,517 | 10/1984 | Rummel | |
| 4,533,369 | 8/1985 | Okita | |
| 4,539,357 | 9/1985 | Babear | 524/267 |
| 4,562,091 | 12/1985 | Sachder et al. | 427/41 |
| 4,621,029 | 11/1986 | Kawaguchi | 428/447 |
| 4,639,379 | 1/1987 | Asai et al. | 427/40 |
| 4,642,246 | 2/1987 | Jansen et al. | 427/127 |
| 4,655,222 | 4/1987 | Florez et al. | 606/219 |
| 4,720,521 | 1/1988 | Spiedvagrt et al. | 524/862 |
| 4,799,484 | 1/1989 | Smith et al. | 606/223 |
| 4,806,430 | 2/1989 | Spielvogel et al. | 428/450 |
| 4,844,986 | 7/1989 | Karakelle et al. | 428/447 |
| 4,849,264 | 7/1989 | Pekar et al. | 427/388.1 |

FOREIGN PATENT DOCUMENTS 62-101236  5/1987  Japan ...................... 606/223

OTHER PUBLICATIONS

Dow Corning Bulletin: 51–599A (Jul. 1986).

*Primary Examiner*—Gary Jackson

[57] ABSTRACT

A siliconized surgical needle is provided which requires significantly less force to effect tissue penetration than a standard siliconized needle.

23 Claims, No Drawings

SILICONIZED SURGICAL NEEDLE AND METHOD FOR ITS MANUFACTURE

This is a continuation of U.S. application Ser. No. 08/144,930 filed Oct. 28, 1993, now abandoned, which is a continuation of U.S. application Ser. No. 08/023,734 filed Feb. 22, 1993, now issued as U.S. Pat. No. 5,258,013, which is a continuation of U.S. application Ser. No. 07/638,169 filed Jan. 7, 1991, now abandoned.

BACKGROUND OF THE INVENTION

This invention relates to a surgical needle possessing a silicone resin coating providing reduced tissue penetration force and to a method for manufacturing the needle.

The siliconization of metallic cutting edges of such articles as razor blades, hypodermic needles, scissors, scalpels and currettes has been known for some time.

U.S. Pat. No. 3,574,673 discloses the silicone coating of a cutting edge employing a siliconization fluid containing a mixture of copolymerizable silicones made up of an aminoalkyl siloxane, specifically a (polyaminoalkyl) alkoxysilane, and a dimethylpolysiloxane.

Dow Corning Corporation's Bulletin 51-599A (July 1986) describes Dow Corning® MDX4-4159 Fluid for siliconizing cutting edges such as those previously mentioned with an ambient temperature and humidity-curable mixture of aminoalkyl siloxane and a cyclosiloxane dissolved in a mixture of Stoddard solvent and isopropyl alcohol. It is recommended that the fluid be applied by dipping, wiping, spraying, etc., in the form of a dilute organic solution, 2 e.g., prepared with a solvent such as hexane, trichlorotrifluoroethane, 1,1,1-trichloroethane or mineral spirits.

U.S. Pat. No. 4,720,521 describes a film-forming siloxane composition for application to the aforementioned cutting edge articles which contains a mixture of three reactive siloxanes together with a non-reactive lubricating siloxane polymer.

SUMMARY OF THE INVENTION

It is an object of the invention to provide a siliconized surgical needle and method for siliconizing a surgical needle in which the needle exhibits an average tissue penetration force below that of a standard siliconized surgical needle.

It is a particular object of the invention to provide a surgical needle with an adherent silicone coating derived from a siliconization material comprising an aminoalkyl siloxane and at least one other siloxane such as a cyclosiloxane which is copolymerizable therewith.

It is another particular object of the invention to provide a siliconization method to be carried out upon a surgical needle possessing an axial bore, or recess, for receiving the tip of a suture, the siliconization method omitting the step of occluding the bore with water as a preliminary to the application of the siliconization material to the needle.

In keeping with these and other objects of the invention, there is provided a siliconized surgical needle exhibiting an average tissue penetration force which is less than the average tissue penetration force of a standard siliconized needle.

A siliconized needle in accordance with this invention can be obtained by applying to a surface of the needle a siliconization material comprising an aminoalkyl siloxane and at least one other silicone copolymerizable therewith and thereafter curing the siliconization material to provide an adherent silicone coating on the needle.

The expression "standard siliconized surgical needle" as used herein refers to a commercially available siliconized surgical needle, e.g., the siliconized surgical needles marketed by Ethicon, Inc., Somerville, N.J.

While the amount of force required to achieve penetration of tissue during suturing may initially be about the same for both the siliconized surgical needle of this invention and a standard siliconized surgical needle and while both needles will tend to experience an increase in penetration force with each successive passage through tissue, at the conclusion of any given number of such passages, the needle of this invention will exhibit significantly less penetration force than the standard needle. Stated another way, the siliconized needle of this invention will retain its initial tissue penetration characteristics to a greater extent than a standard siliconized needle. This reduced tissue penetration force is advantageous inasmuch as it reduces the effort required in the suturing operation, a particular benefit in those cases involving extensive wound closure.

DESCRIPTION OF THE PREFERRED EMBODIMENTS

The surgical needles which can be siliconized in accordance with this invention can be manufactured from a variety of metals such as Series 400 and Series 300 stainless steels. Other suitable metals for the fabrication of surgical needles include the quaternary alloys disclosed in U.S. Pat. Nos. 3,767,385 and 3,816,920, the contents of which are incorporated by reference herein. A particularly preferred quaternary alloy possesses the ranges of components set forth in Table I as follows:

TABLE I

| COMPOSITION OF SURGICAL NEEDLE QUATERNARY ALLOY (WT. %) | | | |
|---|---|---|---|
| Component | Broad Range | Preferred Range | Most Preferred Range |
| Nickel | 10–50 | 24–45 | 30–40 |
| Cobalt | 10–50 | 25–45 | 30–40 |
| Nickel + Cobalt | 50–85 | 60–80 | 65–75 |
| Chromium | 10–30 | 12–24 | 15–22 |
| Molybdenum, tungsten and/or niobium (columbium) | 5–20 | 8–16 | 10–13 |

A particular quaternary alloy within Table I which can be utilized for the siliconized needle of this invention, designated MP35N, is available in wire form from Maryland Specialty Wire, Inc., Cockeysville, Md. and contains (nominal analysis by weight): nickel, 35%; cobalt, 35%; chromium, 20% and molybdenum, 10%.

The siliconization material employed herein and the procedure used in its application will be such as to provide a siliconized surgical needle exhibiting a significantly reduced tissue penetration force compared with that of a standard surgical needle after an equivalent number of passages through the same, or substantially the same, tissue. Advantageously, the average tissue penetration force of the siliconized needle herein will be less than about 10 percent, preferably less than about 20 percent and still more preferably less than about 30 percent, of the average tissue penetration force of a standard siliconized needle after from 5 to 20 passes through the same or similar tissue.

In general, application of a curable siliconization material containing an aminoalkyl siloxane and at least one other copolymerizable siloxane, e.g., an alkyl polysiloxane or a cyclosiloxane, to a surgical needle followed by curing will provide a siliconized-surgical needle meeting the requirements of this invention.

One suitable method for achieving siliconization herein utilizes the siliconization material and procedures described in U.S. Pat. No. 3,574,673, the contents of which are incorporated by reference herein. The siliconization material includes (a) from about 5–20 weight percent of an aminoalkyl siloxane of the formula

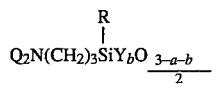

in which R is a lower alkyl radical containing no more than about 6 carbon atoms; Y is selected from the group consisting of —OH and —OR' radicals in which R' is an alkyl radical of no more than 3 carbon atoms; Q is selected from the group consisting of hydrogen, —$CH_3$ and —$CH_2CH_2NH_2$; a has a value of 0 or 1, and b has a value of 0 or 1 and the sum of a+b has a value of 0, 1 or 2, and (b) from about 80 to 95 weight percent of a methyl substituted siloxane of the formula

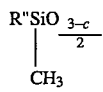

in which R" is selected from the group consisting of —OH and —$CH_3$ radicals and c has a value of 1 or 2.

In addition to, or in lieu of, the foregoing second copolymerizable siloxane, one can use one or more cyclosiloxanes, e.g., as described in the "Encyclopedia of Polymer Science and Engineering", Mark et al., eds, 2nd ed., John Wiley & Son (1989), vol. 15, p. 207 et seq., the contents of which are incorporated by reference herein, provided, of course, the total amount of second copolymerizable siloxane(s) is within the aforestated range.

A particularly preferred siliconization material for use herein is Dow Corning Corporation's Dow Corning® MDX 4-4159 Fluid ("MDX Fluid"), a 50 percent active solution of dimethyl cyclosiloxanes and dimethoxysilyldimethylaminoethylaminopropyl silicone polymer in a mixture of Stoddard solvent (mineral spirits) and isopropyl alcohol. MDX Fluid can be applied to a surface of the cleaned surgical needle by dipping, wiping, spraying, etc., in the form of a dilute organic solution, e.g., prepared with a solvent such as hexane, trichlorotrifluoroethane, 1,1,1-trichloroethane or mineral spirits. In general, it is preferred to dilute MDX Fluid (or other siliconization material) in a hydrocarbon solvent possessing from 5 to 10 carbon atoms, e.g., pentane, hexane (which is preferred), heptane, octane, etc. MDX Fluid cures at room temperature to provide an adherent silicone coating.

After evaporation of any diluent or solvent carrier, the siliconization material is cured to the desired degree. The material can be cured by heating for a short time, e.g., 30 minutes at 120° C., or by exposure to ambient temperature and humidity conditions for longer periods of time.

As previously mentioned, where an axially bored surgical needle is concerned, it is preferred to siliconize the needle employing a procedure which does not require the preliminary step of temporarily occluding the bore. Typically, when siliconizing such a needle by dipping or total immersion in the siliconization material, it has been found necessary to occlude the bore with a liquid, e.g., water, which is immiscible with the siliconization material and thus prevents any of such material from entering the bore where it might interfere with proper attachment of the suture. It has been found that the bore-occluding step can be totally omitted by applying the siliconization material to the needle by spraying. Accordingly, spraying is a preferred method of application of the siliconization material at least in the case of a needle possessing an axial bore, or recess.

Spraying is also the preferred method for applying siliconization fluid to a needle possessing a reduced shank end which is intended to be attached to the tip of a suture employing a shrinkable tubular connector as disclosed in commonly assigned copending U.S. patent application Ser. No. 07/413,240, filed Sep. 27, 1989, the contents of which are incorporated by reference herein. If is preferred in the case of such a needle to insert the needle shank end—first into a support block, e.g., of rigid foam, and thereafter to spray the siliconization fluid onto the exposed surface of the needle. Since the shank end of the needle is embedded in the support block, it will remain free of silicone during the spraying procedure. The use of a support block can, of course, also be employed in the case of the axial recess type needle described above to prevent siliconization material from entering the recess. It is preferable that the coated needle while still in its support block be subjected to curing conditions; if this involves heat, it will, of course, be necessary to select a support block material which can withstand the elevated temperature selected for curing.

The following examples are illustrative of the siliconized surgical needle of this invention and the method for its manufacture.

EXAMPLE 1

This example illustrates the coating of a quantity of surgical needles made from 0.039 inch diameter surgical grade stainless steel wire configured as a ½ circle curved taper point general surgical needle having a length of 37 millimeters (Needle A). Each needle possessed an axial recess at its blend end for receiving the tip of a suture.

The needles were placed in a basket and immersed in an ultrasonic cleansing unit for 5 minutes. The basket was raised to the vapor section of the unit and held there for another 5 minutes. The needles were then dried and after 20 minutes were transferred to a second basket which was immersed for 30 seconds in a siliconization medium prepared from 1 part by volume of MDX Fluid and 9 parts by volume of hexane as solvent. Following drainage of excess siliconization medium, the needles were spread on a tray and heated for 16 hours at 120° C. to effect curing of the silicone coating.

EXAMPLE 2

This example compares the penetration characteristics of Needle A of Example 1 with a commercial siliconized surgical needle of the same diameter and configuration, specifically, Ethicon Inc.'s CT-1 surgical needle (Needle B).

Needle A was tested by passing 78 samples of the needle through a Porvair (Inmont Corporation), a microporous polyurethane membrane of about 0.042 inches thickness which served to simulate flesh. The amount of force in grams to achieve penetration of the Porvair by the needle was measured for each of ten successive penetrations for each of the 78 needle samples. Measurement of the needle penetration force was accomplished using the test procedure and apparatus described in commonly assigned copending U.S. patent application Ser. No. 07/541,055, filed Jun. 20, 1990, the contents of which are incorporated by reference herein. The test was performed by a testing fixture and an Instron Universal Testing Machine. The surgical needles were mounted in a gripping clamp which fixed the needle in a position perpendicular to the Porvair surface and oriented on its radial profile with the axis of rotation on the same plane as the plane of the Porvair. The needle was rotated into the Porvair which was mounted on top of an Instron load cell. The maximum amount of vertical force is recorded as the needle is pushed through the Porvair.

Needle B was tested in the same way as Needle A except that 73 individual needle samples were evaluated.

The average penetration force for all needles measured with each successive passage through Porvair and the average penetration force of the needles after all ten passages through Porvair are set forth in Table I as follows:

TABLE I

Needle Penetration Force Average Penetration Force (gm)

| Passage Through Porvair | 1 | 2 | 3 | 4 | 5 | 6 | 7 | 8 | 9 | 10 | Average of 10 Successful Passages |
|---|---|---|---|---|---|---|---|---|---|---|---|
| Needle A | 196 | 278 | 326 | 373 | 396 | 411 | 429 | 450 | 477 | 484 | 381 |
| Needle B | 207 | 284 | 393 | 490 | 603 | 657 | 681 | 732 | 747 | 791 | 557 | the siliconization method employed in Example 1 where siliconization fluid tended to migrate into the axial recess formed in the blunt end of the needle, there was a much reduced tendency of the fluid to enter the recess when applied by the spraying procedure of this example. Thus, spraying appears to be a more advantageous technique for applying siliconization material to the needle so as it tends to minimize or avoid the presence of silicone in the needle recess, a material which might interfere with proper suture attachment.

Employing the needle penetration force testing procedure described in Example 2, the following penetration data were obtained:

TABLE II

Needle Penetration Force Average Penetration Force (gm)

| Passage Through Porvair | 1 | 2 | 3 | 4 | 5 | 6 | 7 | 8 | 9 | 10 | Average of 10 Successful Passages |
|---|---|---|---|---|---|---|---|---|---|---|---|
| Needle A | 143 | 154 | 181 | 215 | 253 | 289 | 312 | 328 | 358 | 417 | 260 |

As these data show, although the average penetration force of both sets of Needles A and B was about the same upon the first passage of the needles through Porvair, and with each successive passage, greater force was required to achieve penetration, from the third penetration to the last, the tenth, penetration, Needle A required less force to effect penetration than Needle B and the average penetration force for all ten passes through Porvair in the case of Needle A was 30% less than that required for Needle B.

EXAMPLE 3

This example illustrates the siliconization of 10 samples of Needles A of Example 1 employing a spraying procedure. Prior to spraying, the needles were ultrasonically cleaned as in Example 1 and transferred to a tray where they laid on their sides. The siliconization fluid of Example 1 was sprayed onto the needles employing a spray bottle and the fluid was allowed to spread evenly over the needles' surfaces for a period of about 30 minutes. Thereafter, the needles were baked to cure the siliconization fluid. Unlike

What is claimed is:

1. A method for manufacturing a siliconized surgical needle comprising
    a) providing a surgical needle possessing a suture top receiving axial recess in its blunt end;
    b) placing the needle in a ultrasonic cleaning unit having a vapor section;
    c) moving the needle to the vapor section of the unit;
    d) removing the needle from the ultrasonic cleaning unit;
    e) applying a curable siliconization material upon the needle while its recess is unoccluded, there being no significant amount of the siliconization material entering the bore;
    f) allowing the siliconization material to spread evenly over the needle's surface; and
    g) curing the siliconization material on the needle to provide a silicone coating thereon.

2. The method of claim 1, wherein applying is selected from the group of wiping and spraying.

3. The siliconized surgical needle of claim 2 wherein the silicone coating on the needle is obtained from a siliconization material comprising an aminoalkyl siloxane, a cyclosiloxane and at least a hydrocarbon solvent selected from the group consisting of hexane and heptane.

4. The method of claim 1 wherein the shank end of the needle is embedded in a support material during the applying step.

5. The method of claim 1 wherein the siliconization material comprises an aminoalkyl siloxane and at least one other siloxane.

6. The siliconized surgical needle of claim 5 wherein the silicone coating on the needle is obtained from a siliconization material comprising an aminoalkyl siloxane, at least one other siloxane copolymerizable therewith and at least on hydrocarbon solvent of from 5 to 10 carbon atoms.

7. The method according to claim 5 wherein the needle after siliconization exhibits less than about a 100% increase in penetration force after about 5 successive passes through a microporous polyurethane membrane about 0.042 inches thick.

8. The method of claim 7 exhibiting less than about a 77% increase in penetration force after about 5 successive passes through a microporous polyurethane membrane about 0.042 inches thick.

9. The siliconized surgical needle of claim 7 exhibiting an average tissue penetration force after 10 successive passages of less than about 500 grams.

10. The siliconized surgical needle of claim 9 wherein the uncoated needle possesses a diameter of about 0.039 inches.

11. The siliconized surgical needle of claim 7 wherein the needle is fabricated from an alloy comprising nickel, cobalt, chromium and at least one metal selected from the group consisting of molybdenum, tungsten and niobium.

12. The siliconized surgical needle of claim 11 wherein the needle is fabricated form (sic) an alloy comprising from about 10 to about 50 weight percent nickel, from about 10 to about 50 weight percent cobalt with the combined weight of nickel and cobalt being from about 50 to about 85 weight percent, from about 10 to about 30 weight percent chromium and from about 5 to about 20 weight percent of at least one metal selected from the group consisting of molybdenum, tungsten and niobium.

13. The method of claim 7 wherein the silicone coating on the needle is obtained from an aminoalkyl siloxane and an alkyl polysiloxane.

14. The method of claim 7 wherein the silicone coating on the needle is obtained from an aminoalkyl siloxane and a cyclosiloxane.

15. The method of claim 5 wherein the needle exhibits less than about a 200% increase in penetration force after about 10 successive passes through a microporous polyurethane membrane about 0.042 inches thick.

16. The method of claim 15 wherein the needle after siliconization exhibits less than about a 150% increase in penetration force after about 10 successive passes through a microporous polyurethane membrane about 0.042 inches thick.

17. A method for manufacturing a siliconized surgical needle possessing a shank of reduced diameter which comprises embedding the shank in a support material, spraying a curable siliconization material upon the exposed surfaced of the needle and thereafter curing the siliconization material on the needle to provide a silicon coating thereon.

18. The method of claim 17 wherein the siliconization material comprises an aminoalkyl siloxane and at least one other siloxane.

19. The method of claim 18 wherein the silicone coating on the needle is obtained from a siliconization material comprising an aminoalkyl siloxane and a cyclosiloxane.

20. The method of claim 18 wherein the silicone coating on the needle is obtained from a siliconization material comprising an aminoalkyl siloxane, at least one other siloxane copolymerizable therewith and at least one hydrocarbon solvent of from 5 to 10 carbon atoms.

21. The method of claim 20 wherein the silicone coating on the needle is obtained from a siliconization material comprising an aminoalkyl siloxane, a cyclosiloxane and at least one hydrocarbon solvent selected from the group consisting of hexane and heptane.

22. The method of claim 17 wherein the needle is fabricated from an alloy comprising nickel, cobalt, chromium and at least one material selected from the group consisting of molybdenum, tungsten and niobium.

23. The method of claim 17 wherein the needle is fabricated from an alloy comprising from about 10 to about 50 weight percent nickel, from about 10 to about 50 weight percent cobalt with the combined weight of nickel and cobalt being from about 50 to about 85 weight percent, from about 10 to about 30 weight percent chromium, and from about 5 to about 20 weight percent of at least one metal selected from the group consisting of molybdenum, tungsten and niobium.

\* \* \* \* \*